United States Patent
Sugihara et al.

(10) Patent No.: US 6,746,690 B2
(45) Date of Patent: Jun. 8, 2004

(54) PROCESS FOR PRODUCING COMPOSITE PREPARATION CONTAINING NUCLEIC ACID

(75) Inventors: Katsuhiro Sugihara, Nagaokakyo (JP); Junzo Seki, Ibaraki (JP); Kazuko Hirabayashi, Kyoto (JP)

(73) Assignee: Nippon Shinyaku Co., Ltd. (JP)

( * ) Notice: Subject to any disclaimer, the term of this patent is extended or adjusted under 35 U.S.C. 154(b) by 0 days.

(21) Appl. No.: 10/294,865

(22) Filed: Nov. 14, 2002

(65) Prior Publication Data
US 2003/0091622 A1 May 15, 2003

Related U.S. Application Data

(62) Division of application No. 09/701,072, filed on Nov. 20, 2000, now Pat. No. 6,545,138.

(30) Foreign Application Priority Data

May 25, 1998 (JP) ........................................... 10-142763

(51) Int. Cl.$^7$ ................................................ A61K 9/127
(52) U.S. Cl. ........................ 424/450; 514/44; 536/23.1
(58) Field of Search .......................... 424/450; 514/44; 536/23.1

(56) References Cited

U.S. PATENT DOCUMENTS 6,383,512 B1 * 5/2002 Ciccarelli et al. ........... 424/450
2002/0082237 A1 * 6/2002 Sullivan et al. ............... 514/44

* cited by examiner

*Primary Examiner*—David Guzo
(74) *Attorney, Agent, or Firm*—Greenberg Traurig LLP; Eugene C. Rzucidlo

(57) ABSTRACT

A method for producing a composition including a nucleic-acid-containing complex is characterized in that two single strand nucleic acid polymers which can at least partly form double strands are separately mixed, in a single strand form, with a cationic carrier or with source materials for the cationic carrier before the cationic carrier is formed. The resulting mixture is then dispersed in water during the production process of the nucleic-acid-containing complex.

12 Claims, 1 Drawing Sheet

PROCESS FOR PRODUCING COMPOSITE PREPARATION CONTAINING NUCLEIC ACID

This application is a divisional application of application number 09/701,072, filed Nov. 20, 2000 now U.S. Pat. No. 6,546,138, which claims the benefit of PCT/JP99/02713 filed May 24, 1999.

FIELD OF THE INVENTION

The present invention relates to complex preparations which contain a complex of cationic carriers and nucleic acid polymers. This complex is sometimes called a lipoplex.

As used herein, the term "cationic carriers" refers to drug carriers having positive charges in water and effective for transferring drugs, especially transferring anionic drugs into cells. Cationic carriers have been recently studied as drug carriers for the transfer of genes and RNA such as poly I:C into cells.

"Nucleic acid polymers" refer to naturally occurring or synthesized or semi-synthesized polynucleotides (DNA, RNA), and to naturally occurring or synthesized or semi-synthesized oligonucleotides.

BACKGROUND OF THE INVENTION

Nucleic-acid-containing complex preparations that contain a complex of a cationic carrier and a polyanionic double strand nucleic acid polymer having a double helical structure can be produced by only mixing the cationic carrier and the double strand nucleic acid polymer.

However, in the nucleic-acid-containing complex preparations produced by this method, the resulting particles are generally coarse with diameters ranging from a few micrometers to several hundred micrometers, and are heterogeneous. These nucleic acid containing nucleic-acid-containing complex preparations, with their coarse and heterogeneous particles, make it difficult to obtain data for homogeneous preparations in studies on intracellular transfers and signal expressions of nucleic acid polymers. The most critical problems concerning particle coarseness are that sterilization is difficult on an industrial scale and that potential embolizations and the like may occur in capillaries and injection needles or capillaries during intravenous administrations despite the pharmaceuticals being prepared on assumption that they are safe for administration to humans. These problems are difficult problems to solve not only by methods in which the complex preparations are produced by mixing as described above, but also in production methods that apply a dispersion process using appropriate emulsifying dispersion devices.

Another problem is aggregation of the particles resulting from freeze-drying to stabilize the complex preparations.

Nucleic acid polymers in the complex preparations are preferably highly concentrated in order to decrease the dosages and reduce the burden to patients and medical workers at the time of administration as well as in order to achieve productive efficacy of the complex preparations. However, by conventional processes when the total amount of nucleic acid polymers is 0.1 mg/mL or more, especially 0.5 mg/mL or more, aggregation occurs during the production process methods which yields large precipitates of suspended solids, easily grossly confirmed with the naked eye. These precipitates are incapable of being dispersed sufficiently by any dispersion process.

Conventionally, double strand RNA having double helical structures, such as poly I:C, have been commonly employed as genes and RNA from the view of their physiological features and stability for various nucleases. For example, it has been known that sufficient pharmacological efficacy is not obtained by the separate administration of poly I and poly C instead of poly I:C, which has physiological activities such as a strong induction potency of interferon and immunopotentiating actions (Archives of Virology, 51, 199–215 (1976)). Thus, double strands having double helical strand structures, such as poly I:C, are believed to be essential for genes and RNA.

For nucleic-acid-containing complex preparations which contain a complex of cationic carriers and nucleic acid polymers, the necessity for double helical structures has not been discussed at all, and double strand DNA and double strand RNA having the double helical structure have been commonly employed in production procedures of the complex preparations.

The present applicants have applied for the patent for the nucleic-acid-containing complex preparations as nuclease activating preparations in cancer cells since nucleic-acid-containing complex preparations consisting of cationic carriers and double strand RNA such as poly I:C activate nucleases in cancer cells that are effective for the treatment of cancers, and have already applied for the patent for the nucleic-acid-containing complex preparations as therapeutic agents for hepatitis since they induce effective amounts of interferons specifically for the liver and spleen for a long time (PCT/JP98/04695, PCT/JP99/01438).

DISCLOSURE OF THE INVENTION

The objective of the present invention is, in particular, to provide a production method for homogenous nucleic acid containing complex preparations with good quality characterized in that the preparations are capable of being preformed with sterilized by so-called sterilizing filtration and do not contain coarse particles of diameter greater than or equal to 7 $\mu$m, which are considered to be unsafe for administration to humans.

The present inventors were the first to discover that the above problems can be solved without having an effect on their pharmacological activities. The invention involves preparing nucleic acid polymers with a single strand that have been separated from a double helical structure or initially formed without a double strand structure, but without using double strand DNA or and double strand RNA usually having double helical structures, in a production process of nucleic-acid-containing complex preparations which contain a cationic carrier and nucleic acid polymers.

Therefore, the present invention can include a production method of the nucleic-acid-containing complex preparations characterized in that two single strand nucleic acid polymers which can at least partly form double strands are separately added, in a single strand form, to a cationic carrier or source materials for a cationic carrier, and the two single strand nucleic acid polymers are dispersed during the production process of the said nucleic-acid-containing complex preparation that contains a cationic carrier and nucleic acid polymers (referred to as "nucleic-acid-containing complex preparations" hereinafter).

The present invention will be described in detail below.

"Cationic carriers" applicable to the present invention can include drug carriers disclosed in PCT WO94/19314 such as 2-o-(2-diethylaminoethyl) carbamoyl-1,3-o-dioleoyl glycerol (referred to as "compound A" hereinafter) represented as the following structural formula [☐], drug carriers formed by phospholipids as essential components, and drug carriers such as polylysine, in addition to commercially available drug carriers such as lipofectin (brand name), lipofectoamine (brand name), lipofectoace (brand name), and DMRIE-C (brand name).

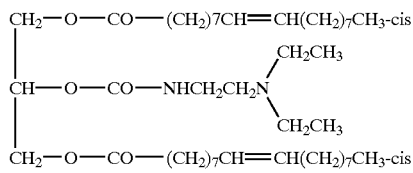

"Two single strand nucleic acid polymers" applicable to the present invention can include, for example, two single strand DNA and RNA polymers which construct natural genes or artificially modified genes (e.g. plasmid), and two single strand RNA polymers such as poly I and poly C, poly I and poly C12U, poly I with partially chemical modification (e.g. poly (7-deazainosinic acid)) and poly C, poly I and poly C with partially chemical modification (e.g. poly (bromocytidylic acid), poly(thiocytidylic acid)). The invention is not limited to these examples if the nucleic-acid polymers are two single strand nucleic acid polymers which can at least partly form double strands. The present invention can be applied to two single strand RNA such as poly I and poly C which construct poly I:C with physiological activities such as a strong induction potency of interferons. As used herein, "poly I", "poly C", "poly A", "poly U", and "poly C12U" mean polyinosinic acid, polycytidylic acid, polyadenylic acid, polyuridylic acid, and copolymer of cytidylic acid and uridylic acid where one uridylic acid is substituted for about every 12 cytidylic acids, respectively.

"Can at least partly form double strands" refers to those polynucleotides which exist as two single stranded complementary nucleic acid polymers that are so aligned that they can form double strands at physiological conditions. The extent to which the polymers at least partly form double strands varies depending on base sequences of the two single strand nucleic acid polymers and the length of each polymer. In general, the number of complementary bases is 20 or more.

The numbers of bases contained in each single strand nucleic acid polymer are, but are not especially limited thereto, suitably 10,000 or less, and preferably 2,000 or less. The numbers of the bases can be appropriately selected depending on the base sequence of each nucleic acid polymer. In addition, the two single strand nucleic acid polymers are not necessarily composed of the same number of bases. Each nucleic acid polymer usually exists with a distribution of various numbers of bases, but "each number of bases" means the number of bases for a distributed maximum and herein refers to an "average base number".

Further, for example, the average base number of poly I and poly C in the present invention can be determined based on a balance between efficacy and safety. Specifically, it is suitable to be in the range of 30 to 3,000 bases, preferably in the range of 60 to 2,000 bases, and more preferably in the range of 100 to 500 bases.

Phospholipids in drug carriers (cationic carriers) formed by the above compound A and phospholipids as essential components are not limited if they are pharmaceutically acceptable. For example, they include phosphatidyl choline, phosphatidyl ethanolamine, phosphatidyl inositol, phosphatidyl serine, sphingomyelin, and lecithin. In addition, hydrogenated phospholipids can be included. Preferred phospholipids can include vitellineegg yolk phosphatidyl choline, egg yolkvitelline lecithin, soy lecithin, and egg yolkvitelline phosphatide. Two or more kinds of phospholipids can be used. Yet, among these cationic carriers, phosphatidyl choline or lecithin are superior to phosphatidyl ethanolamine when used in cationic carriers.

The component ratio of phospholipids to the compound A is varied depending on kinds of the phospholipids and kinds of the applied two single strand nucleic acid polymers. However, the phospholipids are appropriately comprised in the range of 0.1 to 10 weight parts, preferably in the range of 0.5 to 5 weight parts, and more preferably in the range of 1 to 2 weight parts per 1 weight parts of the compound A. This ratio is similar when the phospholipid is replaced by lecithin.

The component ratio of nucleic acid polymers to a cationic carrier varies depending on the source of the cationic carrier and the nucleic acid polymer used. However, the total amount of nucleic acid polymers is appropriately in the range of 0.05 to 10 weight parts, preferably in the range of 0.1 to 4 weight parts, and more preferably in the range of 0.5 to 2 weight parts per 10 weight parts of the cationic carrier. Similarly, when the complex is formed by poly I and poly C with the cationic carrier made of the compound A and phospholipids as essential components, provided that the two single strand nucleic acid polymers are poly I and poly C, the total amount of poly I and poly C is appropriately in the range of 0.05 to 10 weight parts, preferably in the range of 0.1 to 4 weight parts, and more preferably in the range of 0.5 to 2 weight parts per 10 weight parts of the cationic carrier.

The nucleic-acid-containing complex preparations of the present invention (referred to as "present invention preparations" hereinafter) can be produced by conventional methods, for example, by a dispersion process using appropriate emulsifying dispersion machines, after adding the two single strand nucleic acid polymers sequentially or simultaneously to an aqueous solution in which a commercially available cationic carrier is dispersed, or to an aqueous solution in which source materials for a cationic carrier are dispersed. The present invention preparations can also be produced by processes wherein the two single strand nucleic acid polymers are added to a solid cationic carrier or its source materials, adding water, and then dispersing the mixture by an appropriate emulsifying dispersion machine. The sequences to be added, volumes to be added, concentrations to be added, and concentrations of cationic carriers and their source materials in solutions are optionally selected and are not especially limited in the present invention.

More specifically, when using a cationic carrier made of compound A and phospholipids as essential components, the present invention preparation can be prepared by the emulsifying dispersion process wherein the mixture is formed by gradually dripping the aqueous solutions of poly I and poly C separately into the aqueous solution in which the cationic carrier is dispersed. The present invention preparation can also be prepared by the process wherein the compound A, phospholipid, poly I and poly C are weighed and placed in a beaker, roughly dispersed with a homogenizer after the addition of water, and then further dispersed with a pressurized emulsifying dispersion machine.

Two single strand nucleic acid polymers obtained by separating a double strand nucleic acid polymer by conventional manipulations may be used. Specifically, the manipulations can include non-enzymatic treatments such as heating at 60° C. or more, or enzymatic treatments.

The above-described commercially available cationic carriers can be used without processing or with appropriate processing.

The above aqueous solutions can include injectable water, injectable distilled water, and electrolyte solutions such as saline, and glucose solution.

The above emulsifying dispersion machines can include, for example, a homomixer, a homogenizer, an ultrasonic dispersing machine, an ultrasonic homogenizer, a high-pressurized emulsifying dispersion machine, a Microfluidizer (brand name), a Nanomizer (brand name), a Ultimizer (brand name), a DeBEE2000 (brand name), and a Manton-Gaulrin type high-pressurized homogenizer. However, those appropriately employed for medical uses are sufficient. Processing conditions and time periods, and processing temperatures are selected appropriately.

The present invention preparations may contain pharmaceutically acceptable additives, for example, emulsifying dispersion auxiliarys, stabilizers, isotonic agents, lyoprotectantsfreeze-drying auxiliary, and pH adjusters at appropriate amounts. Specifically, those can include fatty acids having from 6 to 22 carbon atoms (e.g. caprylic acid, capric acid, lauric acid, myristic acid, palmitic acid, stearic acid, oleic acid, linoleic acid, arachidonic acid, and docosahexaenoic acid), pharmaceutically acceptable salts thereof (e.g. sodium salts, potassium salts, and calcium salts), emulsifying dispersion auxiliaries such as albumin and dextran, stabilizers such as cholesterol and phosphatidic acid, isotonic agents such as sodium chloride, glucose, maltose, lactose and sucrose, lyoprotectants freeze-drying auxiliaries, and pH adjusters such as hydrochloric acid, sulfuric acid, phosphoric acid, acetic acid, sodium hydroxide, potassium hydroxide, and triethanolamine.

The above-mentioned described pharmaceutically acceptable optional additives may be added in appropriate processes before or after dispersion.

After dispersion, the preparations can be optionally filtered through a 0.2 μm sterilizing filtration membrane filter, and then packaged into ampoules and vials. Particle diameters of almost all of the present invention preparations are 200 nm or less. Therefore, approximately 100% of the present invention preparations can pass through the 0.2 μm sterilizing filtration membrane filter.

By the above-mentioned described production methods of the present invention, nucleic-acid-containing complex preparations containing homogenous and fine complex particles can be obtained, and further, nucleic-acid-containing complex preparations containing nucleic acid polymers in the solution at 0.1 mg/mL or more can be obtained.

Therefore, the nucleic-acid-containing complex preparations obtained by the above-mentioned production methods and the nucleic-acid-containing complex preparations obtained by the above production methods and comprising nucleic acid polymers in concentrations in the solution in a range of 0.1 to 10 mg/mL, in a range of 0.5 to 10 mg/mL, in a range of 1 to 10 mg/mL or in a range of 2 to 10 mg/mL can also be included in the present invention. Yet, the present invention does not exclude nucleic acid polymers with concentrations in solutions at 10 mg/mL or more.

Additionally, if the present invention preparations, produced by dispersion as described above, are freeze-dried, there can be freeze-dried preparations of the present invention. Therefore, the freeze-dried preparations can be also included in one of the present invention preparations. Freeze-drying can be carried out by conventional methods.

The freeze-dried preparations of the present invention can be, for example, freeze-dried by preliminarily freezing in conditions from about −40 to −20° C. for 2 hours after dispensing into vials, followed by a primary drying from about 0 to 10° C. under reduced pressure, and then by a secondary drying from about 15 to 25° C. under reduced pressure. Generally, the inside of the vials is filled with nitrogen gas, and the vials are plugged to obtain the freeze-dried preparations of the present invention. When freeze-drying, the use of lyoprotectants, freeze-drying auxiliaries which form freeze-dried cakes, is preferred. Especially, saccharides and disaccharides are suitable, with maltose being the most preferred.

The freeze-dried preparations of the invention can be reconstituted dissolved by the addition of an appropriate solution (reconstituting dissolving solutions) and used thereafter. These reconstituting dissolving solutions can include injectable water, glucose solution, electrolyte solutions such as saline solutions, and the other infusion solutions. Fluid volumes of these reconstituting solutions vary depending on use and are not especially limited, but 0.5 to 2 fold of the fluid volume before drying or 500 mL or less are appropriate.

The present invention preparations can be provided in the form of liquid formulations such as injectable and drip drugs or in the form of freeze-dried preparations.

The present invention preparations can be administered to animals as well as humans by various routes of administration such as intravenously, intra-arterially, subcutaneously, intra-muscularly, by inhalation, nasally drops, ophthalmically, orally, and rectally. The dosing forms and dosages can be appropriately selected according to desire. In addition, the preparations can be used as various reagents and medicines for the cultured cells of animals, plants, mycetes, and bacteria.

BEST MODE FOR CARRYING OUT THE INVENTION

Hereinafter, the present invention will be described in more detail by representative examples, comparative examples and study examples.

The single strand RNA of poly I and poly C each with an average base number of approximately 200 were used as sources in Example 1 to 5. In addition, filtrated sterilization could be carried out successfully without clogging the filters during filtered sterilization with a 0.2 μm membrane filter after the dispersion process in each Example, and the yields of filtrates were in the range of 98% to 102% for all nucleic acid polymers, indicating potential sterilization at approximately 100%.

EXAMPLE 1

Forty grams of maltose dissolved in 100 mL of injectable water was added to 2 g of the compound A and 2 g of purified egg yolk lecithin, mixed by agitation, and dispersed for 5 minutes by means of a homogenizer to obtain a crude dispersion solution of a cationic carrier. The crude dispersion solution was further dispersed for an hour using a small emulsifying dispersion machine for experiments, and supplemented with injectable water to up to 250 mL to obtain the dispersion solution of the cationic carrier. Seventy five mL of aqueous solution containing 250 mg of poly I was added to 250 mL of this dispersion solution with agitation, then 75 mL of aqueous solution containing 250 mg of poly C was added with agitation, and the mixture was further dispersed for an hour using a small emulsifying dispersion machine, followed by sterilization by filtration with a 0.2 μm membrane filter to obtain the present invention preparation.

The average particle diameter of complex particles in this present invention preparation was 138 nm as measured using a particle diameter measuring apparatus (DLS-700, manufactured by Otsuka Electronics Inc. hereinafter, the same is applied) employing a dynamic light scattering method. No particle with a diameter of 1 μm or more was included.

Thereafter, 1 mL of this present invention preparation was dispensed into each vial and processed into a freeze-dried preparation according to conventional methods. The obtained freeze-dried preparation was reconstituted by the addition of 0.9 mL of injectable water. The average particle diameter of complex particles in the reconstituted present invention preparation was 140 nm as measured using the dynamic light scattering method. No particle with a diameter of 1 μm or more was included.

EXAMPLE 2

Four kg of sucrose dissolved in 10 L of injectable water was added to 50 g of the compound A and 30 g of egg yolk phosphatide, and the mixture was dispersed for 10 minutes by means of a Maenton-Gaulrin high-pressured homogenizer followed by supplementing with injectable water to up to 25 L to obtain a dispersion solution of the cationic carrier. Six L of aqueous solution containing 50 g of poly C was added to 20 L of this dispersion solution with agitation, and then 6 L of aqueous solution containing 50 g of poly I was added with agitation. The pH of this dispersion solution was adjusted to 5.5 using hydrochloric acid, and the dispersion solution was further dispersed for 30 minutes by means of a Maenton-Gaulrin high-pressured homogenizer followed by sterilization by filtration with a 0.2 μm membrane filter to obtain the present invention preparation. The average particle diameter of complex particles in the present invention preparation was measured to be 150 nm. No particle with a diameter of 1 μm or more was included.

Thereafter, 20 mL of this present invention preparation was dispensed into each vial and processed into a freeze-dried preparation according to conventional methods. The obtained freeze-dried preparation was reconstituted by the addition of a commercially available 5% glucose infusion solution (500 mL). The average particle diameter of complex particles in the reconstituted preparation was measured to be 151 nm by means of the dynamic light scattering method. No particle with a diameter of 1 μm of more was included.

EXAMPLE 3

Two grams of the compound A, 2 g of soy lecithin, 25 mg of poly I and 25 mg of poly C were taken into a beaker, 20 g of glucose dissolved in 100 mL of injectable water was added to the beaker, then the contents in the beaker were mixed by agitation, and dispersed for 5 minutes by means of a homogenizer. The crude dispersion solution was then dispersed for an hour using a small high-pressurized emulsifying dispersion machine (800 kg/cm2) for experiments, and supplemented with injectable water to up to 400 mL followed by sterilization by filtration with a 0.2 μm membrane filter to obtain the present invention preparation. The average particle diameter of the complex particles in this present invention preparation was 121 nm as measured by the dynamic light scattering method. No particle with a diameter of 1 μm or more was included.

Example 4

Forty grams of maltose dissolved in 100 mL of injectable water was added to 1.2 g of the compound A and 2.0 g of purified egg yolk lecithin, mixed by agitation, and dispersed for 30 minutes by means of a small high-pressurized emulsifying dispersion machine, and then supplemented with injectable water to up to 250 mL to obtain a dispersion solution of the cationic carrier. Seventy five ml of aqueous solution containing 100 mg of poly I and 75 ml of aqueous solution containing 100 mg of poly C were simultaneously gradually dripped into 250 mL of this dispersion with agitation, and further dispersed for 2 hours using a small pressured emulsifying dispersion machine (1,100 kg/cm2) followed by sterilization by filtration with a 0.2 μm membrane filter to obtain the present invention preparation. The average particle diameter of complex particles in this present invention preparation was 124 nm as measured using the dynamic light scattering method. No particle with a diameter of 1 μm or more was included.

When the distribution of particle diameter sizes of this present invention preparation was measured by a particle diameter measuring apparatus (LA-910, Horiba Ltd., hereafter the same is applied) employing a laser diffractive scattering method, the results as shown in FIG. 1 were obtained. According to this result, a peak of the distribution of particle diameter sizes was 139 nm, and no coarse particle was detected.

EXAMPLE 5

Forty grams of maltose dissolved in 100 mL of injectable water was added to 4.8 g of the compound A and 8.0 g of purified egg yolk lecithin, mixed by agitation, dispersed for 30 minutes by means of a small high-pressurized emulsifying dispersion machine, and then supplemented with injectable water to up to 250 mL to obtain a dispersion solution of the cationic carrier. 75 ml of aqueous solution containing 400 mg of poly I and 75 ml of aqueous solution containing 400 mg of poly C were simultaneously gradually dripped into 250 mL of this dispersion solution with agitation, and further dispersed for 2 hours using a small high-pressurized emulsifying dispersion machine (1,100 kg/cm2) followed by sterilization by filtration with a 0.2 μm membrane filter to obtain the present invention preparation. The average particle diameter of complex particles in this present invention preparation was 138 nm as measured using the dynamic light scattering method. No particle with a diameter of 1 μm or more was included.

EXAMPLE 6

One mL of aqueous solution containing 100 μg of commercially available DNA plasmid vector (pMCIneo) was heated in a water bath at 70° C. and agitated for 3 hours. Two mL of dispersion solution containing 2 mg of commercially available lipofectin (brand name) was similarly heated at 70° C. and added to this with agitation, and the mixture was dispersed for 10 minutes at 70° C. using a probe type ultrasonic dispersion machine followed by sterilization by filtration with a 0.2 μm membrane filter to obtain the present invention preparation. The average particle diameter of complex particles in this preparation was 145 nm as measured using the dynamic light scattering method. No particle with a diameter of 1 μm or more was included.

EXAMPLE 7

The single strand RNA of poly I and poly C, both having average base numbers of about 1,500, were used as the sources.

Forty grams of maltose dissolved in 100 mL of injectable water was added to 1.2 g of the compound A and 2.0 g of purified egg yolk lecithin, mixed by agitation, dispersed for 30 minutes by means of a small high-pressurized emulsifying dispersion machine, and then supplemented with injectable water to up to 250 mL to obtain a dispersion solution of the cationic carrier. Seventy five ml of aqueous solution containing 100 mg of poly I and 75 ml of aqueous solution containing 100 mg of poly C were simultaneously dripped into 250 mL of this dispersion solution by agitation, and further dispersed for 2 hours using a small high-pressurized emulsifying dispersion machine (1,100 kg/cm2) followed by sterilization by filtration with a 0.2 μm membrane filter to obtain the present invention preparation. The average particle diameter of complex particles in this preparation was 134 nm as measured by the dynamic light scattering method. No particle with a diameter of 1 μm or more was included.

EXAMPLE 8

A present invention preparation with an average particle diameter of 130 nm was obtained by similar processes as those of Example 7 with a dispersion pressure at 800 kg/cm2 using 200 mg of poly I with an average base number of about 350 and 200 mg of poly C with an average base number of about 350.

EXAMPLE 9

A present invention preparation with an average particle diameter of 150 nm was obtained by similar processes as those of Example 7 with a dispersion pressure at 800 kg/cm2 using 200 mg of poly I with an average base number of about 1,450 and 200 mg of poly C with an average base number of about 1,450.

EXAMPLE 10

A present invention preparation with an average particle diameter of 135 nm was obtained by similar processes as those of Example 7 with a dispersion pressure at 800 kg/cm2 using 400 mg of poly I with an average base number of about 80 and 400 mg of poly C with an average base number of about 80.

Comparative Example 1 (Production by a Conventional Method Corresponding to Example 4)

Forty grams of maltose dissolved in 100 mL of injectable water was added to 1.2 g of the compound A and 2.0 g of purified egg yolk lecithin, mixed by agitation, and dispersed for 30 minutes by means of a small high-pressurized emulsifying dispersion machine, and then supplemented with injectable water to up to 250 mL to obtain a dispersion solution of the cationic carrier. One-hundred-fifty mL of aqueous solution containing 200 mg of double strand poly I:C having approximately 200 base pairs was gradually dripped into 250 mL of this dispersion solution by agitation, and the mixture was further dispersed for 2 hours using a small high-pressurized emulsifying dispersion machine (1,100 kg/cm2) to obtain a comparative preparation. The average particle diameter of complex particles in this comparative preparation was 182 nm as measured by the dynamic light scattering method.

When a distribution of the particle diameter sizes of this comparative preparation was measured by means a laser diffractive scattering method in the same way as that in Example 4, the results as shown in FIG. 2 were obtained. According to this result, a peak in the distribution of particle diameter sizes was 243 nm, however 20% were detected as coarse particles with 3–20 μm in diameters having a peak of 8000 nm in the distribution, indicating a bimodal distribution of the particles.

In addition, when an attempt was made to filter this comparative preparation through a 0.2 μm membrane filter, only 50 mL of the preparation passed through the filter resulting in clogging of the filter so that the sterilization by filtration failed.

Comparative Example 2 (Production by a Conventional Method Corresponding to Example 5)

Forty grams of maltose dissolved in 100 mL of injectable water was added to 4.8 g of the compound A and 8.0 g of purified egg yolk lecithin, mixed by agitation, dispersed for 30 minutes by means of a small high-pressurized emulsifying dispersion machine, and then supplemented with injectable water to up to 250 mL to obtain a dispersion solution of the cationic carrier. One hundred and fifty mL of aqueous solution containing 800 mg of double strand poly I:C having approximately 200 base pairs was gradually dripped into 250 mL of this dispersion solution by agitation, and further dispersed for 2 hours using a small high-pressurized emulsifying dispersion machine (1,100 kg/cm2) to collect a comparative preparation. This comparative preparation was a white precipitable suspension solution, and precipitated with aggregation within 5 minutes after collection. It was similar to a suspension solution of sake lees. The particle diameters could not be measured because their sizes were above the measuring ranges of the dynamic light scattering particle diameter measuring apparatus. Filtration sterilization through a 0.2 μm membrane filter was impossible.

Test Example 1

Biological activity of the present invention preparation obtained from Example 4 and that of the comparative preparation from Comparative example 1 were evaluated by their suppressive effects on proliferation of uterine cervix cancer cells (Hela S3).

In the experiment, HelaS3 cells were seeded in 96-well plates at concentration of 104 cells/well, adhering to the wells after culture for 5 hours or more followed by the adding of each preparation to the culture. The culturing was continued, and the number of viable cells was counted by MTT method 3 days after the addition of the preparations. Inhibition ratios were obtained from the following formula, and the values of IC50 were calculated. The result is shown in Table 1.

IC50=[1–(value of absorbance in the preparation treated-cell group/value of absorbance in the saline treated-cell group)×100%.

TABLE 1

|  | $IC_{50}$ value (ng/mL) |
|---|---|
| Present invention preparation of Example 4 | 8.6 ± 2.5 |
| Comparative preparation of Comparative example 1 | 8.7 ± 1.2 |

The IC50 value was represented as the concentration of total nucleic acid polymers by combining poly I and poly C.

As shown in Table 1, there was no difference in the biological activity between the present invention preparation according to Example 4 and that of the comparative preparation according to the Comparative example 1.

EFFECTS OF THE INVENTION

The present invention has, for example, the following effects.

(1) Homogenous nucleic-acid-containing complex preparations of a high quality without coarse complex particles can be produced.

(2) Homogenous nucleic-acid-containing complex preparations of a high quality which do not substantially comprise coarse complex particles can be produced. This effect is more remarkable at higher concentrations of nucleic acid polymers.

(3) When freeze-dried preparations of nucleic-acid-containing complex preparations produced according to the present invention are reconstituted, nucleic-acid-containing complex preparations equivalent to those before freeze-drying can be reconstructed.

(4) Nucleic-acid-containing complex preparations which can pass through a 0.2 $\mu$m sterilizing filter with approximately 100% efficacy can be provided.

Figure 1:
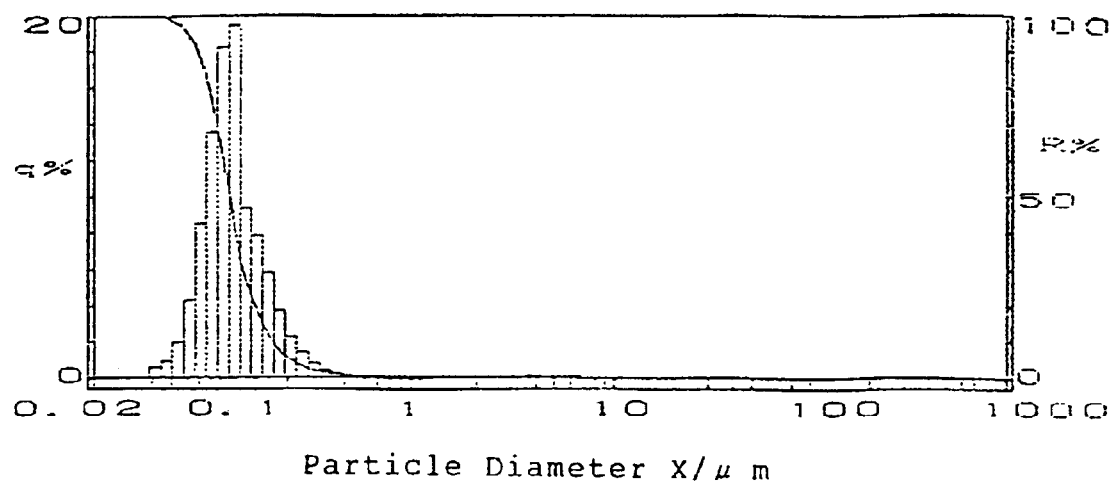
FIG. 1 shows the distribution of the particle diameters of complex particles in the present invention preparation according to Example 4. The horizontal axis, left vertical axis and right vertical axis denote particle diameters ($\mu$m), frequencies (%) and integrated frequencies (%), respectively.
Figure 2:
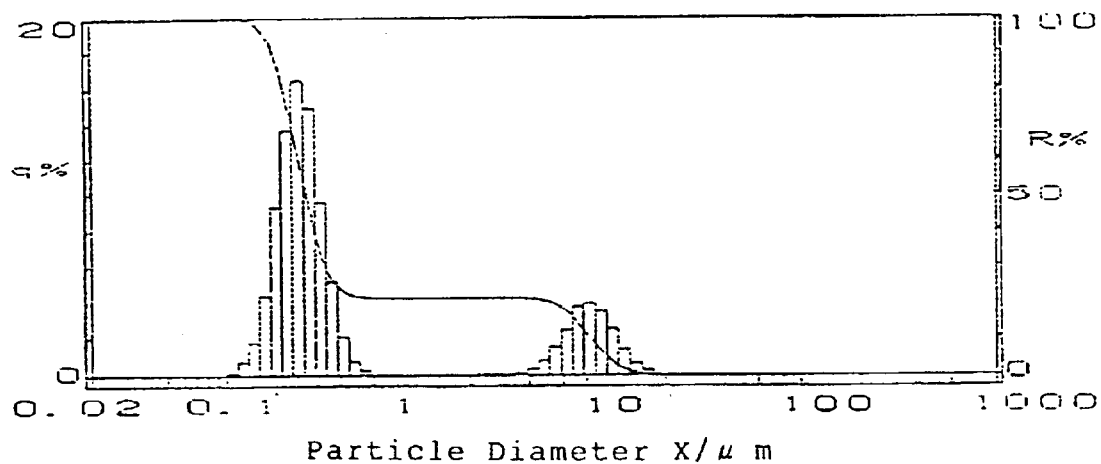
FIG. 2 shows the distribution of the particle diameters of complex particles in the comparative preparation according to Comparative example 1. The horizontal axis, left vertical axis and right vertical axis denote particle diameters ($\mu$m), frequencies (%) and integrated frequencies (%), respectively.

We claim:

1. A composition containing a nucleic-acid-containing complex produced by mixing two single strand nucleic acid polymers which can at least partly form double strands, in a single strand form, with a cationic carrier or with source materials for the cationic carrier before the cationic carrier is formed in an aqueous solution, and dispersing the mixture in an aqueous solution during the production process of the nucleic acid containing complex, wherein the complex comprises a cationic carrier and two single strand nucleic acid polymers which can at least partly form double strands, and wherein an average complex particle size is, no more than about 0.2 $\mu$m in diameter while in a solution state, or a lyophilized composition thereof.

2. The composition of claim 1, or the lyophilized composition thereof, wherein the average complex particle of the composition is no more than about 150 nm in diameter while in a solution state.

3. The composition of claim 1 or the lyophilized composition thereof, wherein the complex particles of the composition are no more than about 200 nm in diameter while in a solution state.

4. The composition according to claim 1 or the lyophilized composition thereof, wherein the concentration of the nucleic acid polymers is in the range of 0.1 to 10 mg/mL in a solution state.

5. The composition according to claim 1 or the lyophilized composition thereof, wherein the concentration of the nucleic acid polymers is in the range of 1 to 10 mg/mL in a solution state.

6. The composition according to claim 2 or the lyophilized composition thereof, wherein the concentration of the nucleic acid polymers is in the range of 0.1 to 10 mg/mL in a solution state.

7. The composition according to claim 2 or the lyophilized composition thereof, wherein the concentration of the nucleic acid polymers is in the range of 1 to 10 mg/mL in a solution state.

8. The composition according to claim 3 or the lyophilized composition thereof, wherein the concentration of the nucleic acid polymers is in the range of 0.1 to 10 mg/mL in a solution state.

9. The composition according to claim 3 or the lyophilized composition thereof, wherein the concentration of the nucleic acid polymers is in the range of 0.1 to 10 mg/mL in a solution state.

10. A composition containing a nucleic-acid-containing complex produced by mixing two single strand nucleic acid polymers which can at least partly form double strands, in a single strand form, with a cationic carrier or with source materials for the cationic carrier before the cationic carrier is formed in an aqueous solution, and dispersing the mixture in an aqueous solution during the production process of the nucleic acid containing complex, wherein the complex comprises a cationic carrier and two single strand nucleic acid polymers which can at least partly form double strands, and wherein the complex particles of the composition can pass through a 0.2 $\mu$m sterilizing filtration membrane filter while in a solution state, or a lyophilized composition thereof.

11. The composition according to claim 10 or the lyophilized composition thereof, wherein the concentration of the nucleic acid polymers is in the range of 0.1 to 10 mg/mL in a solution state.

12. The composition according to claim 10 or the lyophilized composition thereof, wherein the concentration of the nucleic acid polymers is in the range of 1 to 10 mg/mL in a solution state.

* * * * *